United States Patent
Krasikoff et al.

(10) Patent No.: US 9,005,177 B2
(45) Date of Patent: Apr. 14, 2015

(54) ABSORPTIVE BREAST BANDAGE

(71) Applicant: ELN Group, LLC, Cary, IL (US)

(72) Inventors: Nina Krasikoff, Chicago, IL (US); Laurine Sargent, Chicago, IL (US); Eric Ladewig, Cary, IL (US); Lenore McCarthy, Winnetka, IL (US)

(73) Assignee: ELN Group, LLC, Chicago, IL (US)

( * ) Notice: Subject to any disclaimer, the term of this patent is extended or adjusted under 35 U.S.C. 154(b) by 0 days.

(21) Appl. No.: 14/155,574

(22) Filed: Jan. 15, 2014

(65) Prior Publication Data

US 2014/0364825 A1  Dec. 11, 2014

Related U.S. Application Data

(63) Continuation-in-part of application No. 13/913,432, filed on Jun. 8, 2013.

(60) Provisional application No. 61/657,496, filed on Jun. 8, 2012.

(51) Int. Cl.
| | |
|---|---|
| A61F 13/20 | (2006.01) |
| A61F 13/45 | (2006.01) |
| A61F 13/58 | (2006.01) |
| A61L 15/28 | (2006.01) |
| A61L 15/26 | (2006.01) |
| A61L 15/58 | (2006.01) |
| A61F 5/03 | (2006.01) |
| A61F 13/14 | (2006.01) |
| A61F 13/15 | (2006.01) |

(52) U.S. Cl.
CPC .............. *A61F 13/45* (2013.01); *A61F 13/58* (2013.01); *A61L 15/28* (2013.01); *A61L 15/26* (2013.01); *A61L 15/58* (2013.01); *A61F 2013/15016* (2013.01); *A61F 5/03* (2013.01); *A61F 13/14* (2013.01); *A61F 13/141* (2013.01); *A61F 13/145* (2013.01)

(58) Field of Classification Search
CPC .................... A61F 2013/15016; A61F 13/141; A61F 13/145
USPC .................................................. 604/386, 387
See application file for complete search history.

(56) References Cited

U.S. PATENT DOCUMENTS

| | | | | |
|---|---|---|---|---|
| 3,934,593 | A * | 1/1976 | Mellinger | 450/56 |
| 4,530,353 | A * | 7/1985 | Lauritzen | 602/42 |
| 5,919,476 | A * | 7/1999 | Fischer et al. | 424/443 |
| 5,998,693 | A * | 12/1999 | Zagame | 602/52 |
| 7,001,241 | B2 * | 2/2006 | Gorringe et al. | 450/81 |
| 7,905,763 | B1 * | 3/2011 | Frank | 450/37 |
| 8,029,332 | B2 * | 10/2011 | Nadsady et al. | 450/38 |
| 2006/0052033 | A1 * | 3/2006 | Foley et al. | 450/37 |
| 2006/0057938 | A1 * | 3/2006 | Huang | 450/81 |
| 2008/0200096 | A1 * | 8/2008 | Thornton et al. | 450/37 |
| 2009/0299252 | A1 * | 12/2009 | O'Neill | 602/48 |
| 2012/0129428 | A1 * | 5/2012 | Taylor | 450/37 |

* cited by examiner

*Primary Examiner* — Melanie Hand
*Assistant Examiner* — Aundria Hairell
(74) *Attorney, Agent, or Firm* — Tracy Jong Law Firm; Tracy P. Jong; Cheng Ning Jong

(57) ABSTRACT

An absorptive breast bandage adapted to conform to the contours of a human breast. In one embodiment, the absorptive breast bandage comprises a half-moon shaped planar absorbent body configured for absorbing secreted bodily fluids from a post-surgical patient's surgical incision on the human breast. The half-moon shaped absorbent body includes a first surface and a second surface and it is configured to draw the secreted bodily fluids from the post-surgical patient's surgical incision and store the secreted bodily fluids.

9 Claims, 5 Drawing Sheets

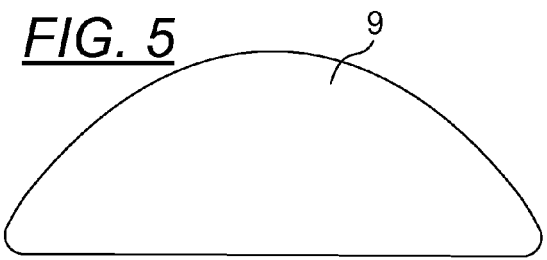
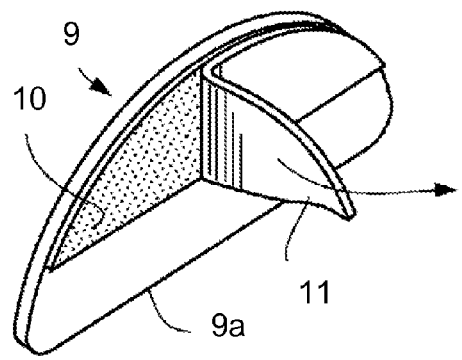
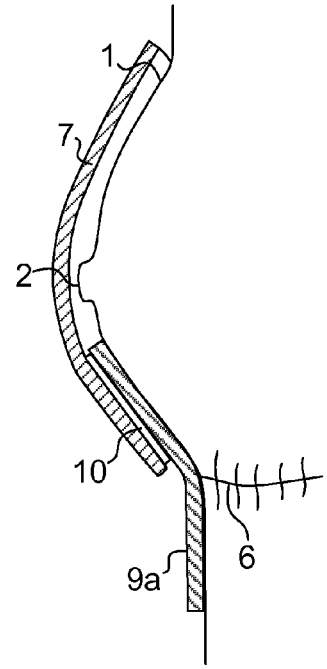
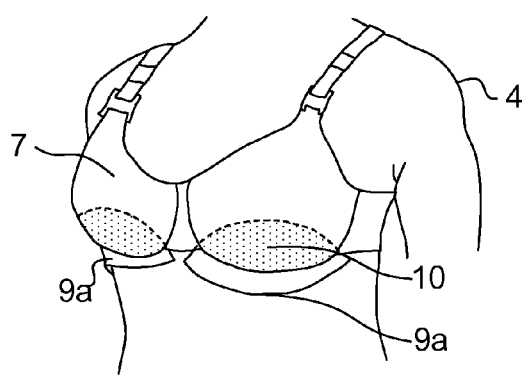

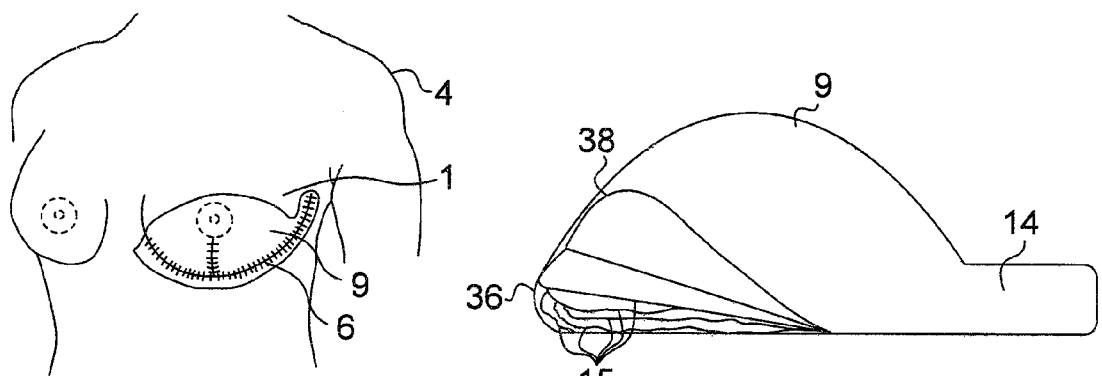
FIG. 14
FIG. 15
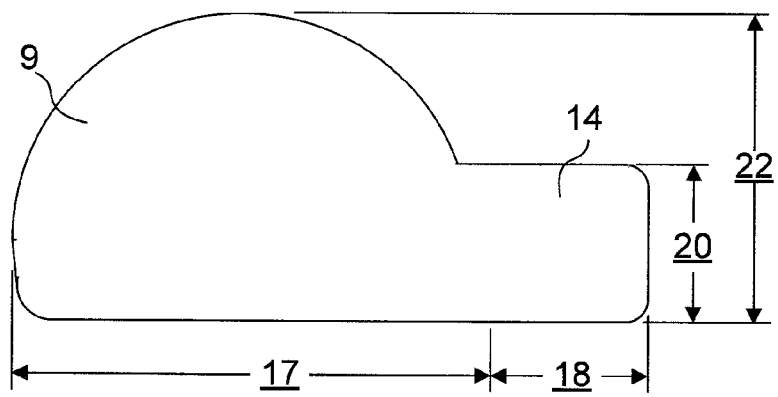
FIG. 16
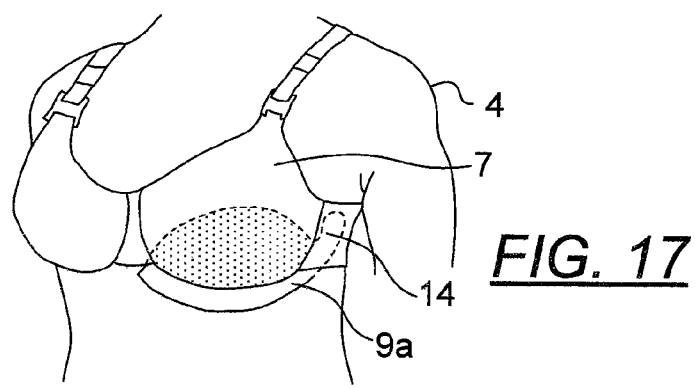
FIG. 17

ABSORPTIVE BREAST BANDAGE

PRIORITY CLAIM AND RELATED APPLICATIONS

This continuation-in-part application claims the benefit of priority from Non-Provisional application U.S. Ser. No. 13/913,432 filed on Jun. 8, 2013 entitled "Medical Bra Assembly for Post-Surgical Breast Reconstruction and Cosmetic Breast Procedures" and U.S. Provisional Patent Application U.S. Ser. No. 61/657,496 filed on Jun. 8, 2012 entitled "Medical Bra Assembly For Post-Surgical Fluid Management." Each of said applications is hereby incorporated by reference herein in its entirety.

BACKGROUND OF THE INVENTION

1. The Field of the Invention

The present invention relates to an absorptive bandage and, more particularly, to an absorptive breast bandage designed to aid and support a patient's post-surgical healing process following breast reconstruction and other types of breast surgical procedures by being able to conform to the curvatures and contours of a patient's breast.

2. Background Art

Conventionally, ubiquitous rectangular shaped bandages are used on wounds of various parts of a human body including those disposed on the breasts. Rectangular bandages are typically used for breast wounds of various stages without regard to the amount of exudates exiting the wounds, the amount of support required on the breast and the comfort afforded by such bandages on the breast. Breast wounds are caused as a result of a mastectomy, cosmetic surgery, breast reduction, breast enhancements, nipple reconstruction and other breast surgical procedures. As there exist many difficulties and frustrations that accompany post-surgical care and procedures, the present absorptive breast bandage makes the application and removal of a bandage on a breast easier and more comfortable. The present absorptive breast bandage further provides support, protection from intrusions, exudate leakage protection, comfort and hygiene, all of which are directed to enhancing the patient's wellbeing and recovery following breast surgery.

The present absorptive breast bandage may be used alone in aiding in a wound healing process or providing comfort to a patient. It may also be used in conjunction with other components in a bra assembly to aid in one of the multiple stages of wound healing. When used with a bra assembly, the present absorptive breast bandage aids in one or more stages of the healing process of a breast surgery.

SUMMARY OF THE INVENTION

Following breast reconstructive surgery and other types of breast surgical procedures, sutures and incisions continue to bleed, weep or otherwise secrete bodily fluids, which make it necessary to absorb these secretions. An attachable absorptive breast bandage accomplishes this function. The absorptive breast bandage is preferably made out soft, clinically and medically approved, highly absorptive materials. The absorptive breast bandage is adapted to conform to the contours of a human breast.

In one embodiment, the absorptive breast bandage comprises a half-moon shaped planar absorbent body including a first surface and a second surface, the half-moon shaped planar absorbent body is configured to draw the secreted bodily fluids from the post-surgical patient's surgical incision on the human breast and store the secreted bodily fluids. The absorptive breast bandage has a peel off adhesive strip on the second surface which can be attached to the lower edge of the bra cup inside surface. The absorptive breast bandage extends below the lower edge of the bra cup and absorbs blood and bodily fluids secreting from the sutures and incisions. In addition, the absorptive breast bandage covers and protects the wound and sutures from rubbing against the lower edge of the bra promoting healing. The bandage is composed of medically and clinically approved lightweight and highly absorbent materials making it easy to fit into the bra cup and can be discretely worn by the patient. In addition, it is attached directly to the bra there is no direct contact to the skin with adhesives eliminating potential skin irritations. The absorptive breast bandage promotes hygiene and keeps the bra fresh and clean. This thin absorptive breast bandage absorbs secretions and can be recyclable, biodegradable and disposable. The absorptive breast bandage provides convenience, comfort and hygiene and helps to prevent infection and combat swelling around sutures and reconstructed breast tissue.

In another embodiment, the absorptive breast bandage further comprises a silicone layer disposed on the second surface for providing structural integrity to the absorptive breast bandage and act as a barrier to prevent collected exudates from staining articles of clothing or bra disposed over the absorptive breast bandage. The absorptive breast bandage further comprises an adhesive portion disposed on a periphery of the first surface for attachment of the absorptive breast bandage directly to the human breast. The adhesive portion is comprised of silicone but is not limited to silicone as any medically or clinically approved adhesive can be utilized.

In yet another embodiment, the absorptive breast bandage further comprises a tail configured to extend a length laterally from a base portion of the absorptive breast bandage. The applicants discovered that for more prominent or longer incisions that extend beyond the breast towards the armpit such as incisions required for lymph node removal, it is impossible to size the width of the half-moon portion of the absorbent body to encompass the entire incision and to maintain the integrity of the proportion of the half-moon required to cover the entire nipple and areola portion of the breast. The present invention meets the need for disposing a bandage for effective absorbance of exudates from wounds and protecting wounds from bra, clothing and other potential irritants by providing an absorptive breast bandage capable to be adapted to conform to the contours of a human breast. The hygienic composition of the present absorptive breast bandage can be worn for prolonged and extended periods of time well after incisions have healed to provide added comfort. In particular, the absorptive breast bandage can be worn to help women dealing with excess body moisture under the breast, a condition which often leads to *Candida* and other yeast infections. It can also be used for many other common breast conditions including the control and prevention of subcutaneous infections (bacterial and fungal), rashes, excessive sweating, general hygiene, and increased comfort of patients with certain body physiques.

Accordingly, it is a primary object of the present invention to provide an absorptive breast bandage capable to be adapted to conform to contours of a human breast that can be easily and expediently applied to a breast without requiring multiple points of attachment and handling of large and ill-shaped bandages.

It is another object of the present invention to provide an absorptive breast bandage to collect exudates from a post-surgical wound and to prevent leakages of such exudates to their surroundings.

It is yet a further object of the present invention to provide an absorptive breast bandage which is discreet, comfortable to wear, and offers suitable protection to the wound area and its surroundings.

It is yet a further object of the present invention to provide an absorptive breast bandage that does not have to be adhered directly to the skin eliminating skin irritations from adhesive tapes.

It is yet a further object of the present invention to provide an absorptive breast bandage that can be easily lifted and reapplied repeatedly without irritation to the skin or compromise to the integrity of the bandage.

Whereas there may be many embodiments of the present invention, each embodiment may meet one or more of the foregoing recited objects in any combination. It is not intended that each embodiment will necessarily meet each objective. Thus, having broadly outlined the more important features of the present invention in order that the detailed description thereof may be better understood, and that the present contribution to the art may be better appreciated, there are, of course, additional features of the present invention that will be described herein and will form a part of the subject matter of this specification.

BRIEF DESCRIPTION OF THE DRAWINGS

In order that the manner in which the above-recited and other advantages and objects of the invention are obtained, a more particular description of the invention briefly described above will be rendered by reference to specific embodiments thereof which are illustrated in the appended drawings. Understanding that these drawings depict only typical embodiments of the invention and are not therefore to be considered to be limiting of its scope, the invention will be described and explained with additional specificity and detail through the use of the accompanying drawings in which:

FIG. 5 is an orthogonal view of an outside surface of one embodiment of the present absorptive breast bandage.

FIG. 6 is a perspective view of an absorptive breast bandage showing an absorbent body, an adhesive portion and a peel-off layer.

FIG. 7 is a partially transparent perspective view of the embodiment of FIG. 6 disposed on a patient.

FIG. 8 is a partial cross-sectional view of the embodiment of FIG. 7, depicting the present absorptive breast bandage adhered to a bra.

FIG. 14 is a partially transparent perspective view of yet another embodiment of the present absorptive breast bandage disposed over post-surgical incisions of a breast.

FIG. 15 is an orthogonal view of the embodiment depicted in FIG. 14, showing the inside layers.

FIG. 16 is an orthogonal view of one embodiment of the present absorptive breast bandage with a tail which is utilized for longer incisions.

FIG. 17 is a perspective view of an application where the absorptive breast bandage of FIG. 14 is covered with a bra.

PARTS LIST

1—Breast
2—Nipple
3—Areola
4—Patient
5—Rectangular Bandage
6—Incision
7—Bra Cup
8—Adhesive Tape
9—Absorptive Breast Bandage
9a—Absorbent Body
10—Adhesive Layer
11—Peel-off Layer
12—Silicone Adhesive Portion
13—Split Release Film
14—Tail
15—Multiple Layers
16—Width of Adhesive
17—Width of Base of Absorptive Breast Bandage with Tail
18—Length of Tail of Absorptive Breast Bandage
20—Height of Tail of Absorptive Breast Bandage
22—Height of Absorptive Breast Bandage with Tail
24—Circle
26—Line Splitting a Circle in Equal Halves
28—Line Parallel to but Disposed at a Line Splitting a Circle in Equal Halves
30—Rounded Corner
32—Radial Offset
34—Radius
36—non-woven rayon with polyester outer layer
38—highly absorbent cellulose layer

PARTICULAR ADVANTAGES OF THE INVENTION

Figure 2:
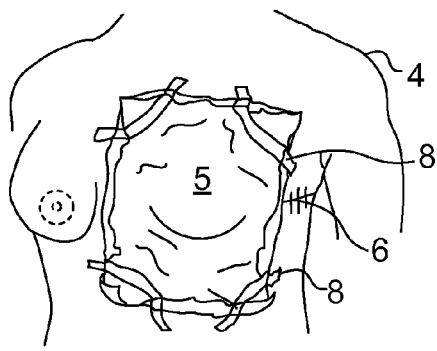
FIG. 2 is a perspective view of a prior art bandage on a human breast with adhesive tape.
Figure 3:
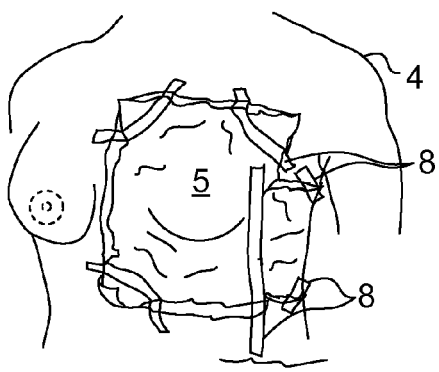
FIG. 3 is a perspective view of multiple prior art bandages on a human breast with adhesive tape.
Figure 4:
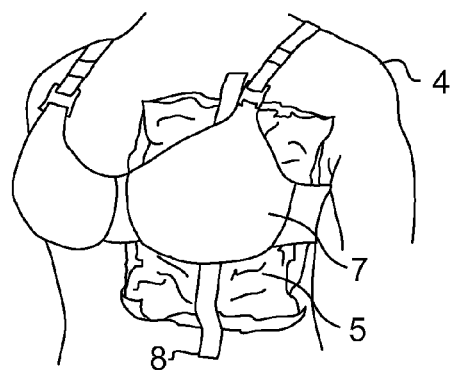
FIG. 4 is a perspective view of an application where the prior art bandage of FIG. 2 is covered with a bra.

The standard shape for prior art post-surgical dressings or bandages is rectangular. Rectangular bandages work well for most applications where the wound surface areas are flat. However they are not well suited for women's anatomical needs, especially at the breast area. The rectangular shaped bandages do not follow the contour and curve of a woman's breast and body. It is akin to fitting a square peg in a round hole. When applied on a breast, prior art bandages do not lie flat and buckle which result in leaking of excess exudates and other fluids or leaving wound exposed when the patient moves. In addition, they are large, bulky and cumbersome, and as a result, do not fit well under women's articles of clothing or bra as shown in FIGS. 2-4.

As such, a need currently exists for a bandage that is specifically designed to fit securely to a woman's breast. A need also exists for a sterile, absorbent bandage that can be worn everyday comfortably and discreetly under a woman's articles of clothing or bra.

The present absorptive breast bandage has a unique ergonomic shape designed to fit the contours of the breast so that it conforms securely to the contours of the breast without buckling and therefore making the bandage more effective in collecting exudates from the wearer. Further, the bandage can be positioned on any part of the breast (side, top, or bottom), making it extremely versatile.

In one embodiment, the present absorptive breast bandage is configured to be directly adhered to a breast, rendering additional securing methods and accessories unnecessary.

In one embodiment, an adhesive portion is disposed about the periphery of the absorptive breast bandage, making an applied bandage of such embodiment capable of containing exudates without leakages.

In one embodiment, the present absorptive breast bandage includes a tail sufficient to cover the most prominent breast wound while enabling the absorbent body of the present absorptive breast bandage to be sized appropriately such that the absorbent body may conform to the contours of a breast. This is in stark contrast to the use of a single or multiple rectangular bandages sufficient to cover the most prominent wound and areas surrounding the wound.

The present absorptive bandage can also be applied to surfaces of a human or non-human body having contours similar to those of the breasts, such as the groin, buttocks, neck, belly, ankle and knee areas, etc.

DETAILED DESCRIPTION OF A PREFERRED EMBODIMENT

The term "about" is used herein to mean approximately, roughly, around, or in the region of. When the term "about" is used in conjunction with a numerical range, it modifies that range by extending the boundaries above and below the numerical values set forth. In general, the term "about" is used herein to modify a numerical value above and below the stated value by a variance of 20 percent up or down (higher or lower).

The term "first surface" is used herein to mean the surface of a present bandage, when applied, faces and comes in contact with a patient or the skin or breast of the patient.

The term "second surface" is used herein to mean the surface of a present bandage, when applied, faces away from a patient, or in one embodiment, comes in contact with a garment worn by the patient.

In order to realize the advantages offered by the present absorptive breast bandage, it is imperative to review conventional practices in wound bandaging of the breasts as shown in FIGS. 1 to 4.

Figure 1:
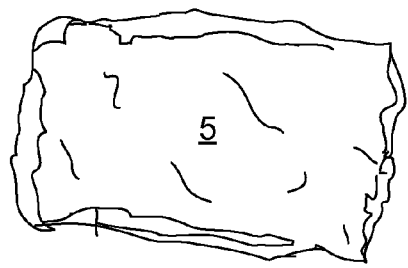
FIG. 1 is a perspective view of a prior art bandage.

FIG. 1 is a perspective view of a prior art bandage 5 showing a rectangular shape typically utilized in post-surgical applications. FIG. 2 is a perspective view of an application of a prior art bandage 5 on a human breast 1 adhered with adhesive tape 8. A large rectangular bandage is first disposed over an entire breast before the bandage is secured with multiple pieces of adhesive tape to the patient 4. As the bandage does not conform to the contours of the breast, wrinkles tend to form, causing parts of the bandage to be raised from the breast and fail to properly collect exudates evenly from the breast. It is impossible to ensure that this prior art bandage is laid close to the skin to which it is meant to cover or protect. Such a large rectangular bandage is inconvenient to handle or to wear as it is bulky and has four corners which significantly extend into the space of other articles of clothing or body parts, i.e., arm, abdomen, etc. The corners also tend to curl and roll to form even more grasping points for articles of clothing to rub against and pull. As a result, accidental detachments of the bandage from its wearer or pulling on the skin of the wound area become prevalent, making for ineffective and uncomfortable applications. In many breast surgeries the incision oftentimes extends underneath the patients arm and requires multiple bandages as the traditional rectangular bandage does not appropriately cover the entire incision 6.

FIG. 3 demonstrates usage of multiple prior art rectangular bandages 5 secured to the breast with adhesive tape 8 to cover the incisions. The prior art rectangular bandages overlap and create extra bulkiness and excess material making its application cumbersome and uncomfortable for the patient.

FIG. 4 is a perspective view of an application where the prior art bandage of FIG. 2 is covered with a bra cup 7. Although the use of a bra over the applied bandages may aid in applying pressure on the bandage against the breast, the bra further increases the bulkiness experienced by the wearer, which now includes both large rectangular bandages 5 and a bra. Due to the size and shape of the rectangular bandages there is unnecessary and excessive bandaging that adds to the bulkiness when worn with a bra. Similar to the practice shown in FIG. 2, the bandage application practice of FIG. 4 also results in all the disadvantages present in FIG. 2.

In FIG. 5, in a preferred embodiment, the absorptive breast bandage 9 comprises a half-moon shaped planar absorbent body configured for absorbing secreted bodily fluids from a post-surgical patient's surgical incision or wound. The half-moon shaped absorbent body includes a first surface and a second surface and it is configured to draw the secreted bodily fluids from the post-surgical patient's surgical incision and store the secreted bodily fluids. In use, the absorbent body is disposed on and/or pressed against an area of the patient including the post-surgical patient's incision such that the absorbent body comes in contact with the surgical incision where exudates exit. The second surface includes a crest portion and a base portion.

FIG. 6 is a perspective view of an absorptive breast bandage 9 showing an absorbent body 9a, an adhesive portion 10, and a peel-off layer 11. An adhesive portion is disposed on the crest portion and is configured to be attachable to a lower portion of an inside surface of a bra cup disposed over the human breast. A peel-off layer 11 is disposed over the adhesive portion until such time when the bandage is ready to be applied on a patient at which time the peel-off layer 11 is removed. In one embodiment, a double coated tape is used as the adhesive portion and includes one surface designed specifically for clothing and another that is adhered directly to the back of the absorptive breast bandage. Such tape is approved for direct contact with clothing without leaving build up or residue and for facilitating application and reapplication of the bandage to a portion of the inside surface of a bra cup.

In FIG. 7, a perspective view of an absorptive breast bandage is disposed in an in-use position in which the absorbent body 9a extends below the lower edge of the bra cup 7. The first post-surgery stage involves a stitched incision at the site of the patient's breast that corresponds to the lower edge of an adjacent bra cup. The absorbent body 9a collects fluid secretions from the patient's wound that might otherwise stain the bra cup or clothing located in the area surrounding the bra cup. The base portion of the bandage is configured to extend below a patient's breast to shield the bottom edge of a bra cup from vertical or horizontal movement (or rubbing) against the sutures and incision, thereby protecting the wound. As the adhesive portion does not come in direct contact with the patient's skin, a patient with sensitive, compromised or at-risk skin may prefer this embodiment as it eliminates the possibility for skin irritation.

Figure 9:
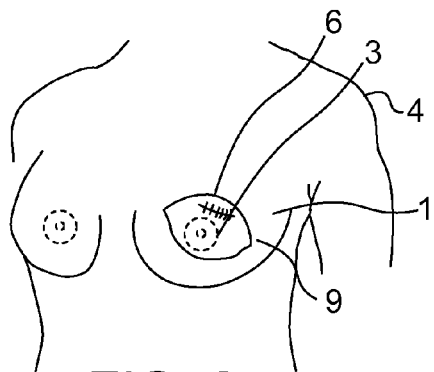
FIG. 9 is a perspective view of one embodiment of the present absorptive breast bandage applied to an incision.

In FIG. 8, an absorptive breast bandage 9 is shown in a side cross-sectional view. As shown, absorptive breast bandage 9 has its peel-off layer removed to expose adhesive portion 10, which is adhered to the lower inside surface of bra cup 7 such that absorptive body 9a extends downwardly from the lower edge of bra cup 7. This protects the sutures and incision 6 from irritation as a result of rubbing against the bra. FIG. 9 is a partially transparent perspective view of yet another embodiment of the present absorptive breast bandage disposed over post-surgical wounds of a breast. In this instance, the incision 6 is disposed above an areola 3. The absorptive breast bandage 9 is applied to the incision with its base covering and protecting the incision and crest covering and protecting the areola area without any excess materials, such as in the case of a rectangular bandage disclosed elsewhere herein. Such wounds can be the outcomes of a breast lumpectomy, biopsy, or other invasive procedures. It is intended for treating low to moderately exuding wounds, such as surgical wounds, cuts and abrasions.

Figure 10:
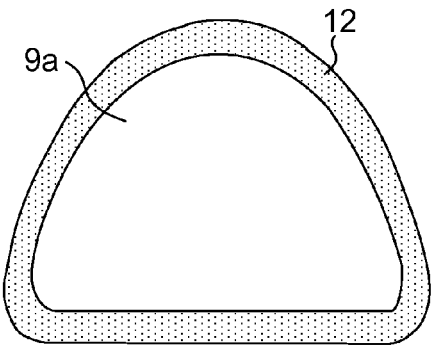
FIG. 10 is an orthogonal view of an embodiment of the present absorptive breast bandage showing an absorbent layer surrounded by an adhesive perimeter.
Figure 11:
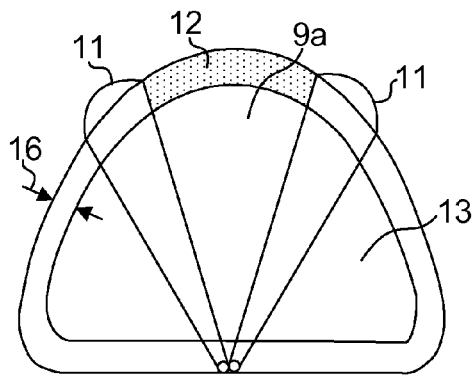
FIG. 11 is an orthogonal view of an absorptive breast bandage showing an absorbent body, an adhesive portion and a peel-off layer.

In FIG. 10, the absorbent body 9 of the absorptive breast bandage is adhered to an adhesive silicone backing which includes a periphery of the first surface for attachment of the absorptive breast bandage to the human breast. In one embodiment, the absorptive breast bandage comprises a silicone layer disposed on the second surface for preventing leakage of the absorbent body through the second surface and containing any fluids within the absorbent body. Silicone is preferred as it is inert and less likely to cause sensitivity reactions in sensitive, compromised or at-risk skin than many other materials used in conventional wound dressings. In addition, the silicone backing makes the product permeable and highly flexible, allowing it to conform well to body contours. In one embodiment, the bandage fabric can be infused with an anti-microbial agent to aid the healing of minor cuts, burns and other skin irritations. FIG. 11 is an orthogonal view of the absorptive breast bandage showing an absorbent body 9a, a silicone adhesive portion 12, and a split release film 13. Two peel off layers 11 comprise the split release film 13 with one layer overlapping another to form a tab at a central location which are substantially symmetrically disposed on the first surface to facilitate removal and reapplication of the peel off layers. The split release film 13 is disposed over the first surface including the peripherally disposed adhesive portion to protect such surface from contamination until it is ready for use. If a bandage is deemed reusable (as it has not been soiled or structurally compromised), the bandage may be removed after its application such that the peel off layer may be again replaced to protect the first surface until such time the bandage is ready for use again. In one embodiment, the width 16 of the adhesive portion 12 is about ½ inch.

Figure 12:
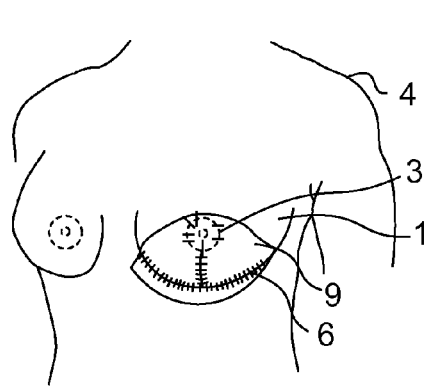
FIG. 12 is a perspective view of one embodiment of the present absorptive breast bandage applied to another incision.
Figure 13:
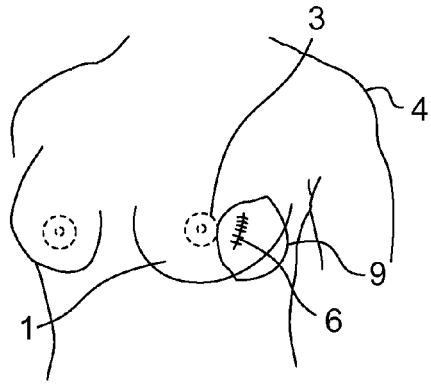
FIG. 13 is a perspective view of one embodiment of the present absorptive breast bandage applied to yet another incision.

FIGS. 12 and 13 depict various types of wounds that may result from a breast surgery and the means by which the present absorptive breast bandage can be used during the recovery period after breast surgery to collect fluids during the healing process. FIG. 12 is a perspective view of one embodiment of the present absorptive breast bandage 9 applied to an incision. The wound, in this case, includes a sutured incision 6 running from the areola 3 of a breast to the bottom edge of the breast and another running from one end of the bottom edge of the breast to the opposite end of the bottom edge of the breast. Such wounds can be the outcomes of a breast reduction procedure, mastectomy procedure and the like. The absorptive breast bandage 9 is arranged with its crest above its base such that the crest covers and protects the entire areola 3 area including the nipple 2 and the bottom edge of the breast in their entirety without any excess materials, such as in the case of a rectangular bandage disclosed elsewhere herein.

FIG. 13 is a perspective view of one embodiment of the present absorptive breast bandage 9 applied to yet another wound. In this instance, the incision 6 is disposed on one side of the breast. The absorptive breast bandage 9 is applied to the wound with its base securely covering and protecting the incision 6 while the crest portion conforms and lies smoothly on the rounded part of the breast with no excess material which would be the case with prior art rectangular bandages. In all instances depicted in FIGS. 12 and 13, the absorptive breast bandage 9 is adapted to conform to contours of a human breast 1.

FIG. 14 is a partially transparent perspective view of yet another embodiment of the present absorptive breast bandage disposed over post-surgical wounds of a breast, suitably covering a breast. This embodiment further comprises a tail 14 which enables prominent incisions 6 to be covered while leaving the crest suitably shaped and sized to cover the entire areola 3 portion of the breast.

FIG. 15 is an orthogonal view of the embodiment of FIG. 14 with its various layers peeled back to reveal the multiple layers 15 comprised of a non-woven rayon with polyester outer layer 36 forming the skin-facing surface and a highly absorbent cellulose layer 38 forming the garment-facing surface.

FIG. 16 is an orthogonal view of the absorptive breast bandage 9 with a tail 14. The tail is configured to extend a length laterally from the base portion. Although the present disclosure shows a tail extending from one side of the base portion, it would have been within the purview of the present invention that a tail may extend from the opposite side of the base portion. The ratio of the width 17 of the base of the absorptive breast bandage with tail to the height 22 of the absorptive breast bandage with tail is about 3:2. Note that the width 17 of the base represents the width of the base of the bandage as if the bandage does not include a tail. Note also that the length 18 of the tail is then the balance of the total width of the bandage. The ratio of the width 17 of the base of the absorptive breast bandage with tail to the length 18 of the tail of the absorptive breast bandage is about 3:1. The ratio of the height 20 of the tail of the absorptive breast bandage to the length 18 of the tail of the absorptive breast bandage is about 1:1.

FIG. 17 is a perspective view of a pair of bra cups 7, with one embodiment of the present absorptive breast bandage 9 placed into the lower inside surface of the bra cup and in which the absorptive layer extends below the lower edge of the bra cup 7. The absorptive breast bandage is contoured to fit discretely and comfortably within the bra covering the entire incision with one bandage as opposed to the bulkiness and clumsiness of traditional rectangular bandages as shown in FIG. 4. Alternatively it can be secured directly to the breast using medical grade adhesive tape.

Figure 18:
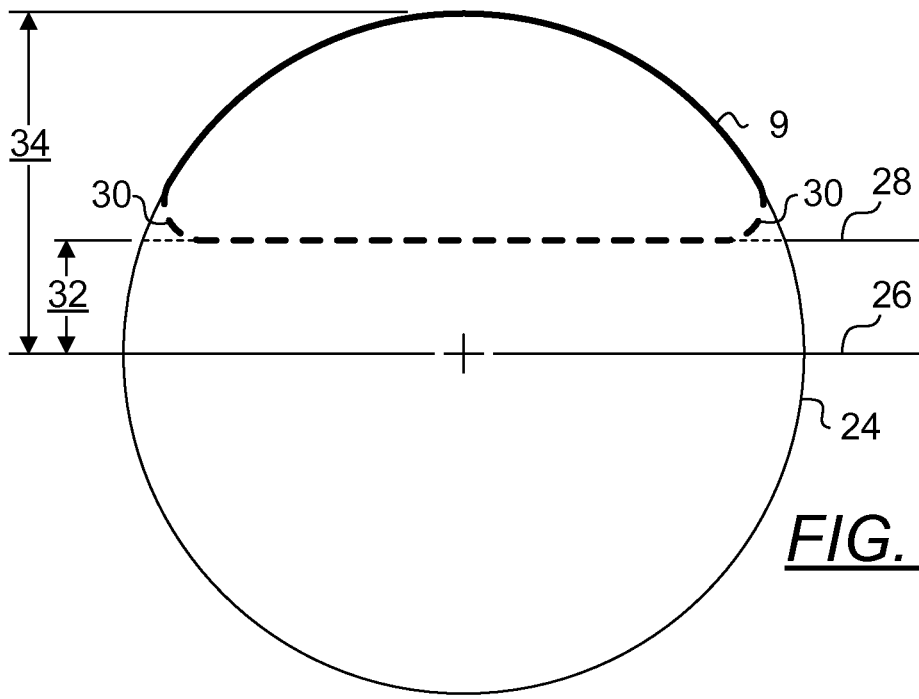
FIG. 18 is an orthogonal view of one embodiment of the means by which the shape of the present absorptive breast bandage is derived.

FIG. 18 is an orthogonal view of one embodiment of the means by which the shape of the present absorptive breast bandage is derived. A line 26 is first drawn through the center of a circle 24, i.e., intersecting the center of the circle 24 to split the circle 24 into two parts. A line 28 parallel to line 26 but disposed at a radial offset 32 is then drawn on one of the two parts to further dissect the part into two. In one embodiment, the ratio of the radial offset 32 to the radius 34 ranges from about 0 to about ½. In a preferred embodiment, this ratio is about 0. The part bounded by a border portion of the circle 24 becomes a shape suitable for use as an absorptive breast bandage. Corners are preferably rounded to form rounded corners 30 to prevent the corners from getting tangled with articles of clothing or bra disposed over the bandage.

Figure 19:
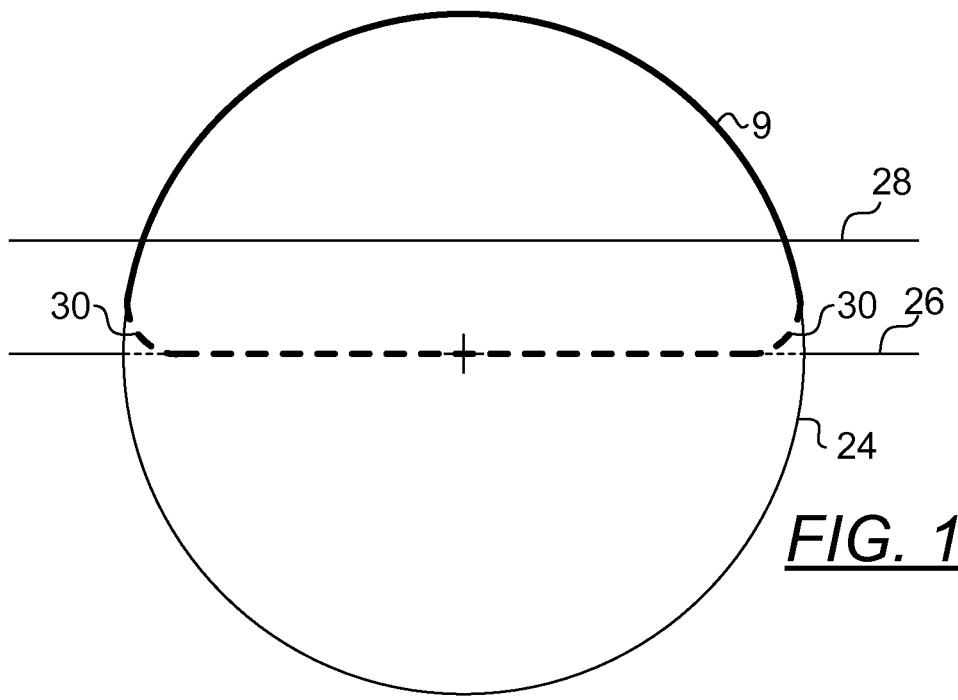
FIG. 19 is an orthogonal view of another embodiment of the means by which the shape of the present absorptive breast bandage is derived.

FIG. 19 is an orthogonal view of another embodiment of the means by which the shape of the present absorptive breast bandage is derived. In this embodiment, the shape is simply a half circle, i.e., the ratio of the radial offset 32 to the radius 34 is zero. In order to realize the advantages offered by the present absorptive breast bandage, it is imperative to review conventional practices in wound bandaging of the breasts as shown in FIGS. 1-4.

While particular elements, embodiments and applications of the present invention have been shown and described, it will be understood, of course, that the invention is not limited thereto since modifications can be made by those skilled in the art without departing from the scope of the present disclosure, particularly in light of the foregoing teachings.

What is claimed is:

1. An absorptive bandage adapted to conform to contours of a skin surface, said absorptive bandage consists of a flat out half-moon shaped absorbent body and an adhesive portion, wherein said flat out half-moon shaped absorbent body includes a skin-facing surface and a garment-facing surface and said half-moon shaped absorbent body is adapted to draw fluids from the skin surface with said half-moon shaped absorbent disposed such that said skin-facing surface faces the skin surface and store the fluids and said garment-facing surface consists of a crest portion and a base portion, said adhesive portion is disposed on only said crest portion.

2. An absorptive bandage adapted to conform to contours of a skin surface, said absorptive bandage consists of a tail, a flat out half-moon shaped absorbent body having a crest portion and a base portion having a width, wherein said half-moon shaped absorbent body has a skin-facing surface and a garment-facing surface and said half-moon shaped absorbent body is adapted to draw fluids from the skin surface with said half-moon shaped absorbent disposed such that said skin-facing surface faces the skin surface and store the fluids and said tail is configured to extend a length laterally from said base portion and the ratio of said width of said base to said length of said tail is about 3:1.

3. The absorptive bandage of claim 2, wherein said half-moon shaped absorbent body comprises a non-woven rayon with polyester outer layer forming said skin-facing surface and a highly absorbent cellulose layer forming said garment-facing surface.

4. An absorptive breast bandage adapted to conform to contours of a human breast, said absorptive breast bandage consists of a flat out half-moon shaped absorbent body and an adhesive portion, wherein said half-moon shaped absorbent body includes a breast-facing surface and a garment-facing surface and said half-moon shaped absorbent body is adapted to draw secreted bodily fluids from a post-surgical incision on the human breast with said half-moon shaped absorbent body disposed such that said breast-facing surface faces the post-surgical incision and store the secreted bodily fluids and said garment-facing surface consists of a crest portion and a base portion, said adhesive portion is disposed on only said crest portion and configured to be attachable to a lower portion of an inside surface of a bra cup disposed over the human breast.

5. An absorptive bandage adapted to conform to contours of a breast surface, said absorptive bandage consists of a tail, a flat out half-moon shaped absorbent body having a crest portion and a base portion having a width, wherein said half-moon shaped absorbent body has a breast-facing surface and a garment-facing surface and said half-moon shaped absorbent body is adapted to draw fluids from a post-surgical incision on the human breast with said half-moon shaped absorbent disposed such that said breast-facing surface faces the skin surface and store the fluids and said tail is configured to extend a length laterally from said base portion and the ratio of said width of said base to said length of said tail is about 3:1.

6. The absorptive breast bandage of claim 5, wherein said half-moon shaped absorbent body comprises a non-woven rayon with polyester outer layer forming said breast-facing surface and a highly absorbent cellulose layer forming said garment-facing surface.

7. An absorptive breast bandage adapted to conform to contours of a human breast, said absorptive breast bandage consisting of a flat out half-moon shaped absorbent body having a breast-facing surface and a garment-facing surface, wherein said half-moon shaped absorbent body has an adhesive portion disposed on the entire periphery of said breast-facing surface for attachment of said absorptive breast bandage to the human breast, wherein said half-moon shaped absorbent body is adapted to draw secreted bodily fluids from a post-surgical incision on the human breast with said half-moon shaped absorbent body disposed such that said breast-facing surface faces the post-surgical incision and store the secreted bodily fluids.

8. The absorptive breast bandage of claim 7, wherein said adhesive portion comprises silicone.

9. The absorptive breast bandage of claim 7, wherein the width of said adhesive portion is about ½ inch.

* * * * *